US010660575B2

(12) United States Patent
MacCallum (10) Patent No.: US 10,660,575 B2
(45) Date of Patent: May 26, 2020

(54) ULTRA HIGH IMPEDANCE SENSOR WITH APPLICATIONS IN NEUROSENSING

(71) Applicant: ZENGAR INSTITUTE INC., Victoria (CA)

(72) Inventor: Kenneth MacCallum, Victoria (CA)

(73) Assignee: Zengar Institute Inc., Victoria (CA)

( * ) Notice: Subject to any disclaimer, the term of this patent is extended or adjusted under 35 U.S.C. 154(b) by 630 days.

(21) Appl. No.: 15/031,229

(22) PCT Filed: Nov. 26, 2014

(86) PCT No.: PCT/CA2014/051133
§ 371 (c)(1),
(2) Date: Apr. 21, 2016

(87) PCT Pub. No.: WO2015/077886
PCT Pub. Date: Jun. 4, 2015

(65) Prior Publication Data
US 2016/0262703 A1    Sep. 15, 2016

Related U.S. Application Data

(60) Provisional application No. 61/910,033, filed on Nov. 27, 2013.

(51) Int. Cl.
*A61B 5/00* (2006.01)
*A61B 5/0428* (2006.01)
(Continued)

(52) U.S. Cl.
CPC ........ *A61B 5/7225* (2013.01); *A61B 5/04004* (2013.01); *A61B 5/0428* (2013.01);
(Continued)

(58) Field of Classification Search
None
See application file for complete search history.

(56) References Cited

U.S. PATENT DOCUMENTS 827,107 A    7/1906  Maynard
4,411,273 A  10/1983 John
(Continued)

FOREIGN PATENT DOCUMENTS

CA    2706956 A1     6/2009
CN  101902958 A    12/2010
(Continued)

OTHER PUBLICATIONS

Ross, C. A., "Recent Patents on Non-Contact Electrodes for Measuring EEG and EKG", Recent Patents on Electrical & Electronic Engineering 2013, 6, 2-6.
(Continued)

*Primary Examiner* — Etsub D Berhanu
(74) *Attorney, Agent, or Firm* — Oyen Wiggs Green & Mutala LLP (57) ABSTRACT

A sensor circuit usable with capacitive sensors in an electrical potential sensing network is provided. The sensor circuit provides bias current while maintaining a high input impedance for signals in a frequency band of interest by positive feedback of a filtered measurement through a finite impedance. The sensor circuits are suited for technologies such as, but not limited to electroencephalography (EEG), electromyography (EMG) and electrocardiograms (ECG). A neurofeedback system utilizing the capacitive conduction sensor is also described.

32 Claims, 7 Drawing Sheets

(51) Int. Cl.
  *A61B 5/04* (2006.01)
  *G01R 19/00* (2006.01)
  *H03F 1/38* (2006.01)
  *G01R 23/165* (2006.01)
  *G01R 23/167* (2006.01)
  *A61B 5/0482* (2006.01)
  *A61B 5/0488* (2006.01)

(52) U.S. Cl.
  CPC .......... *A61B 5/0482* (2013.01); *A61B 5/0488* (2013.01); *A61B 5/04284* (2013.01); *A61B 5/725* (2013.01); *G01R 19/0023* (2013.01); *G01R 23/165* (2013.01); *G01R 23/167* (2013.01); *H03F 1/38* (2013.01); *H03F 2200/261* (2013.01)

(56) References Cited

U.S. PATENT DOCUMENTS

| | | | |
|---|---|---|---|
| 4,503,860 | A | 3/1985 | Sams et al. |
| 5,230,346 | A | 7/1993 | Leuchter et al. |
| 7,088,175 | B2 | 8/2006 | Krupka |
| 7,729,740 | B2 | 6/2010 | Kraus, Jr. et al. |
| 8,193,821 | B2 | 6/2012 | Mueller et al. |
| 8,264,247 | B2 | 9/2012 | Prance et al. |
| 8,780,512 | B2 | 7/2014 | Sullivan |
| 2004/0070446 | A1* | 4/2004 | Krupka .............. G01R 29/0871 330/69 |
| 2004/0155702 | A1 | 8/2004 | Danielsson |
| 2008/0004536 | A1* | 1/2008 | Baxi ................. A61B 5/04288 600/509 |
| 2010/0301418 | A1* | 12/2010 | Kim .................... H01L 27/0262 257/360 |
| 2011/0043225 | A1 | 2/2011 | Sullivan et al. |
| 2011/0046503 | A1 | 2/2011 | Pradeep et al. |
| 2011/0069419 | A1* | 3/2011 | Su .................... G02F 1/136204 361/56 |
| 2011/0282231 | A1 | 11/2011 | Pradeep et al. |
| 2012/0095361 | A1 | 4/2012 | Xu et al. |
| 2012/0250197 | A1 | 10/2012 | Sullivan |
| 2012/0265080 | A1 | 10/2012 | Yu et al. |
| 2013/0039509 | A1 | 2/2013 | Chuang et al. |
| 2013/0066183 | A1 | 3/2013 | Jin et al. |
| 2013/0079659 | A1 | 3/2013 | Akhadov et al. |

FOREIGN PATENT DOCUMENTS

| | | |
|---|---|---|
| CN | 103002800 A | 3/2013 |
| EP | 1451595 B1 | 7/2009 |
| EP | 2442443 A1 | 4/2012 |
| KR | 0079009 A2 | 5/1983 |
| KR | 2012-0102201 A | 9/2012 |
| KR | 2013-0093302 A | 8/2013 |
| WO | 9405201 A1 | 3/1994 |
| WO | 2012158457 A1 | 11/2012 |

OTHER PUBLICATIONS

Campbell, A. et al., "NeuroPhone: Brain-Mobile Phone Interface using a Wireless EEG Headset", MobiHeld 2010.

Sullivan, T. et al., A Low-Noise, Non-Contact EEG/ECG Sensor, IEEE 2007.

Chi, Y.M. et al., "Wireless Non-contact Cardiac and Neural Monitoring", Wireless Health 2010.

Chi, Y.M. et al., "Non-contact Low Power EEG/ECG Electrode for High Density Wearable Biopotential Sensor Networks", Body Sensor Networks 2009.

\* cited by examiner

FIG. 6

ULTRA HIGH IMPEDANCE SENSOR WITH APPLICATIONS IN NEUROSENSING

CROSS-REFERENCE TO RELATED APPLICATION

This application claims priority from U.S. Application No. 61/910,033 filed 27 Nov. 2013. For purposes of the United States, this application claims the benefit under 35 U.S.C. § 119 of U.S. Application No. 61/910,033 filed 27 Nov. 2013, and entitled ULTRA HIGH IMPEDANCE SENSOR WITH APPLICATIONS IN NEUROSENSING which is hereby incorporated herein by reference for all purposes.

FIELD OF THE INVENTION

This invention relates to apparatus for signal detection and related methods. The apparatus has particular application in detecting low-amplitude bioelectrical signals. For example, the apparatus may be used to acquire electroencephalogram ("EEG") signals, electrocardiography (ECG) signals or electromyography (EMG) signals.

BACKGROUND

Biological activity in mammals, including humans, generates electric fields. These fields vary over the body and change depending on physical, emotional, and mental condition. For example, functioning of the brain generates electrical fields that can be detected by monitoring electrical potentials at points on the scalp. The monitored potentials are an example of electroencephalography (EEG) signals. Features of EEG signals such as the frequency spectrum provide an indication of the functioning of the brain. Neurofeedback systems may process EEG signals and generate sounds or other feedback signals. Users may use neurofeedback systems to learn to exercise control over the functioning of their brains.

An example neural feedback system that uses auditory stimulation to provide feedback is the NeurOptimal® system available from Zengar Institute Inc. of Victoria, Canada www.zengar.com. NeurOptimal monitors a user's brainwaves and alerts the central nervous system when it is not functioning smoothly by modulating music that the user is listening to. When brain activity shows signs of turbulence, the music provided by the NeurOptimal® neurofeedback software is momentarily interrupted. This subtle cue alerts the user's brain that it is operating inefficiently. With repeated training sessions, the brain learns to "reset" itself and function more smoothly.

A beating heart also creates a time-varying electric field that can be detected at the skin. The monitored signals are an example of electrocardiography (ECG) signals. One can analyze ECG signals to determine whether the heart beat is normal or abnormal. Similarly, sensors may be placed to measure muscle function using electromyography (EMG).

Patent documents that describe various EEG systems include: U.S. Pat. Nos. 5,230,346; 4,503,860; 4,411,273; 7,729,740; US Publication No. 20110282231; US Publication No. 20110046503; and US Publication No. 20130079659.

Bioelectrical signals including EEG signals are generally small in amplitude. Such signals generally require amplification. As the signals are weak, noise is problematic. The overall performance of a system for monitoring small electrical potentials (for example, EEG, EMG, ECG systems) can be highly dependent on the nature of the sensors used to detect the electrical potentials.

Patent documents that describe sensors which provide amplification include US20130066183, US20120250197, EP1451595B1, and U.S. Pat. No. 8,264,247.

Various types of electrode may be used to detect EEG signals. Some EEG systems use wet-contact electrodes. Wet-contact electrodes are used with conductive gels or pastes to provide low-impedance connections to the user. Wet-contact electrodes can be inconvenient and time consuming to use. Furthermore, conductive gels and pastes are messy and can often bleed between neighboring sensors and cause signal contamination.

Dry electrodes do not use pastes or gels, but rather contact the user directly. The electrical impedance of connections made using dry electrodes is typically much greater than the electrical impedance of connections made using wet contact electrodes. This impedance of connections made with dry sensors can vary significantly due to factors such as skin condition, the presence of hair between the dry electrode and the skin etc.

Non-contact sensors rely on capacitive coupling and do not require an electrically-conductive connection to a subject to operate. There are a number of problems associated with non-contact sensors. The coupling to the field is very weak, making the sensor prone to extraneous noise pickup. Also, typical amplifier designs require finite—although commonly minute—input currents to operate correctly. Non-contact sensors are described, for example, in: Sullivan et al. A Low-Noise, Non-Contact EEG/ECG Sensor IEEE 2007; Cauwenberghs et al. Wireless Non-contact Cardiac and Neural Monitoring. Wireless Health, Oct. 7, 2010. San Diego, USA.; Ross, Recent Patents on Non-Contact Electrodes for Measuring EEG and EKG Recent Patents on Electrical & Electronic Engineering 2013, 6, 2-6; Chi et al., Non-contact Low Power EEG/ECG Electrode for High Density Wearable Biopotential Sensor Networks, Sixth International Workshop on Wearable and Implantable Body Sensor Networks Jun. 3-Jun. 5, 2009. non-contact sensors are also described in U.S. Pat. No. 8,193,821, CA2706956, US20120265080 and U.S. Pat. No. 8,780,512.

US20130039509 and U.S. Pat. No. 827,107 describe headsets equipped with electrodes for detecting bioelectrical signals. EP2709519A1 describes various applications for sensed biosignals. U.S. Pat. No. 7,088,175 describes measuring free space electric fields.

There remains a need for sensors suitable for detecting small electrical potentials that ameliorate some of the disadvantages of existing sensors. In the field of neurosensing and neurofeedback there remains a need for reliable non-contact sensors that can operate in the presence of noise and are suitable for technologies such as electroencephalography (EEG), electromyography (EMG), and electrocardiograms (ECG).

SUMMARY

This invention has a number of aspects. One aspect provides sensor circuits usable as front ends for detecting electrical potentials at one or more sensors. In some embodiments the sensors comprise capacitive sensors. In some embodiments the electrical potentials comprise bioelectrical signals. Another aspect provides EEG systems incorporating such sensor circuits. another aspect provides biofeedback systems incorporating such circuits. Another aspect provides a method of operation of a sensor circuit to provide bias current for an input amplifier and/or to cancel noise signals resulting from electrostatic discharges.

One example aspect provides apparatus for measuring electrical potentials in a frequency band of interest. The apparatus comprises an amplifier having an input and an output; a filter having an input connected to receive a signal from the amplifier output and an output; and an impedance having a resistive component coupled between the filter output and the amplifier input. The filter has a passband that excludes direct current signals and the amplifier and filter combined have unity gain for signals in a frequency band within the passband of the filter.

Another example aspect provides a method for detecting electrical potentials. The method comprise sat an output of an amplifier having an input coupled to an electrical potential, detecting an amplifier output signal comprising a signal of interest; extracting the signal of interest from the amplifier output signal; and applying the extracted signal of interest to one end of an impedance having a second end connected to the amplifier input. The signal of interest may be a signal within a specified frequency band and extracting the signal of interest may comprise filtering the amplifier output signal.

Another example aspect provides a neurosensing system comprising two or more capacitive sensors, each coupled to a corresponding amplifier input. For each of the corresponding amplifier inputs an impedance is connected between the amplifier input and a point driven at a potential equal to a signal of interest comprising a difference between a corresponding amplifier output signal and a virtual ground potential. The virtual ground potential may be s an average of potentials of the two or more capacitive sensors.

Another example aspect provides a neurofeedback system. The neurofeedback system comprises: an electrical potential sensing system, a processor and a neurofeedback module. The electrical potential sensing system comprises at least two pairs of capacitive conduction sensors, each pair comprising a first circuit for a first sensor and a second circuit for a second sensor. The first and second circuits comprise an input to provide a voltage in, an amplifier to provide a voltage out, the amplifier in electrical communication with a differential circuit, the differential circuit in electrical communication with a filter, the filter providing a bandwidth limited output of the amplifier, the filter in electrical communication with an impedance. The impedance provides an output, the output returning between the input and the amplifier. The first circuit and the second circuit are in electrical communication with each other at the differential circuits, to provide a bias current cancellation and a virtual driven ground. The processor comprises instructions for processing a subtraction signal from the electrical potential sensing system and instructions for the neurofeedback system. The neurofeedback module is configured to provide a sensory output.

Further aspects and example embodiments are illustrated in the accompanying drawings and/or described in the following description.

BRIEF DESCRIPTION OF THE DRAWINGS

The accompanying figures illustrate non-limiting example embodiments of the invention.

DEFINITIONS

Amplifier—Amplifier means a circuit or device that presents at an output a signal that, at least within a range of operating frequencies, is essentially the same as a signal presented at an input multiplied by a gain G. G is not limited to being larger than one but may be larger than, equal to, or smaller than one. G may be positive or negative.

BPF—Bandpass Filter.
IC—Integrated Circuit.
PCB—Printed Circuit Board.
LPF—Low-Pass Filter.
FFT—Fast Fourier Transform—A method for numerically determining the frequency content of a sampled signal.

DETAILED DESCRIPTION

Figure 1:
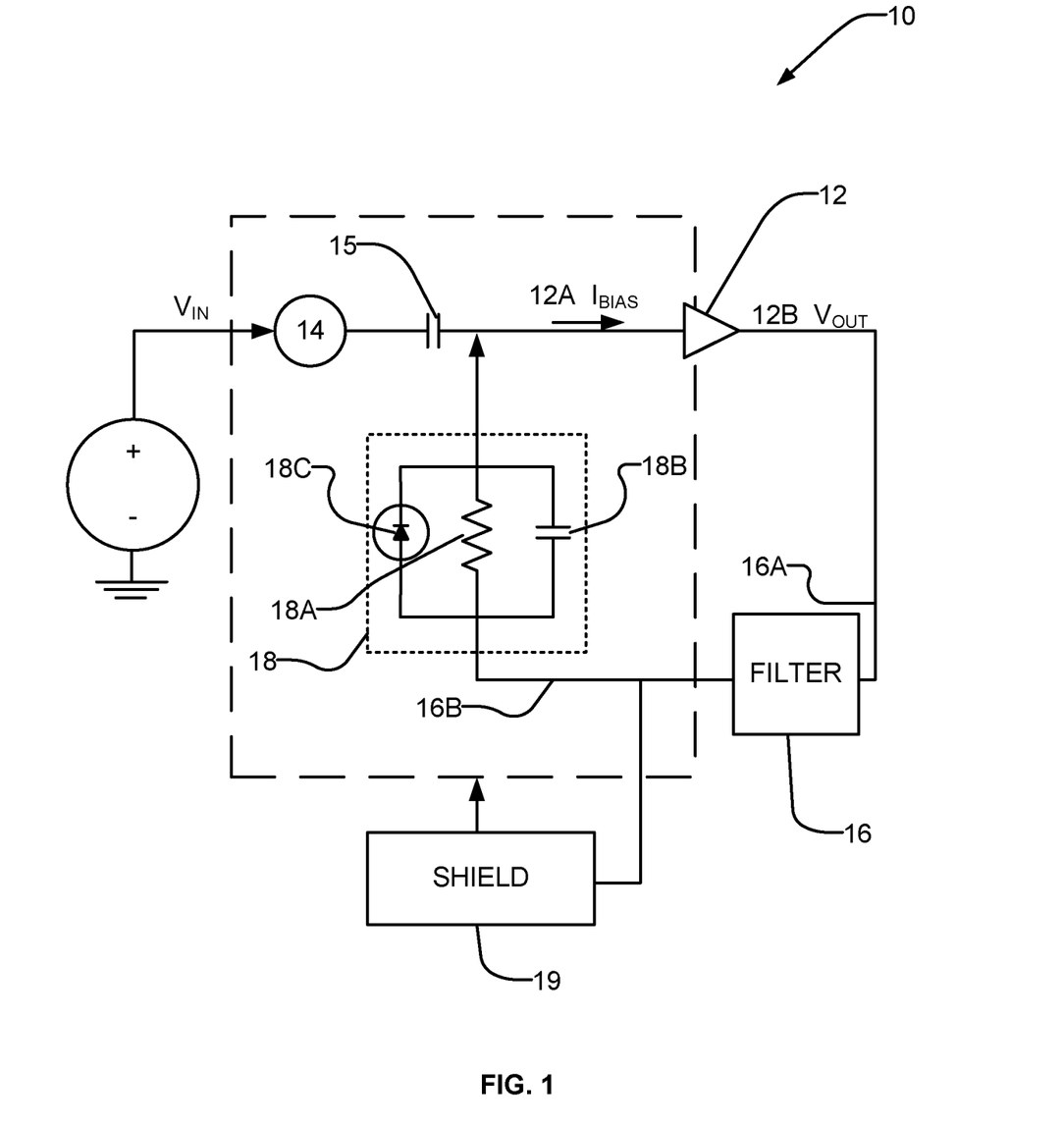
FIG. 1 is a circuit diagram for a single sensor.

FIG. 1 shows a sensor circuit 10 according to an example embodiment. Sensor circuit 10 is designed to detect electrical signals within a frequency band of interest. In an example embodiment the frequency band of interest includes frequencies above some cut-off frequency. The cut-off frequency may be in the milliHertz range (e.g. 100 mHz or so). In an example embodiment the frequency band of interest is 100 mHz to 100 Hz, or 1 kHz or so. This frequency band is a frequency band useful in certain EEG applications. The precise upper and lower bounds of the frequency band of interest are not critical. Other frequency bands may be of interest in other applications.

Sensor circuit 10 comprises an amplifier 12 having an input 12A and an output 12B. Input 12A is connected to a sensor 14 which may, for example, comprise an electrode in proximity to the skin of a subject. It is unnecessary for the electrode to be in conductive contact with the subject's skin. The sensor may comprise a dry electrode or a non-contact electrode, for example.

Amplifier 12 has a high input impedance to facilitate sensing small changes in electrical potential at the subject's skin notwithstanding the fact that sensor 14 does not make good or even any conductive contact with the subject's skin. Amplifier 12, may, for example, comprise a conventional amplifier such as an operational amplifier. In some embodiments, amplifier 12 comprises an operational amplifier in a unity gain configuration, Circuit 10 includes a capacitor 15 between sensor 14 and amplifier 12. Capacitor 15 may be provided by capacitance of sensor 14 and/or by a separate component. Providing a capacitor 15 as a separate component provides the added safety advantage of ensuring that circuit 10 cannot supply direct current to the subject unless capacitor 15 fails.

Circuit 10 includes circuitry for correcting charge imbalances at the input of amplifier 12. Because amplifier 12 has a high input impedance and capacitor 15 also presents a high impedance to direct currents electrical charge can build up at the input of amplifier 12. The charge build up can be caused by the bias current required by amplifier 12 (shown as $I_{BIAS}$) which, although it may be tiny (in the range of picoamperes or femtoamperes in some cases) is not zero. Electrostatic discharges can also cause electric charge to build up at the input of amplifier 12.

Circuit 10 is configured to provide a relatively low-impedance pathway to address charge imbalances at input 12A of amplifier 12 at one or more frequencies outside the frequency band of interest while maintaining a high impedance for all frequencies within the frequency band of interest. This is achieved by the combination of a filter 16 and an impedance 18 connected between an output 16B of filter 16 and the input 12A of amplifier 12. The input 16A to filter 16 is connected to the output 12B of amplifier 12. Impedance 18 comprises a resistor in a simple case. Other cases are described below. The electrical resistance of impedance 18 may be much lower than the input impedance of amplifier 12. For example, in some embodiments, amplifier 12 may have an input impedance of $10^9$ ohms or more while impedance 18 has a resistance on the order of $10^7$ ohms or so. The exact value for the resistance of impedance 18 is not critical. In some embodiments the resistive component of the impedance of impedance 18 is significantly lower than a resistive component of the impedance of the connection between input 12A of amplifier 12 and the subject. In some embodiments the resistive component of the impedance of impedance 18 is significantly lower than a resistive component of the impedance of any other connection to the input 12A of amplifier 12.

The gains of amplifier 12 and filter 18 are selected such that, for signals within the frequency band of interest, the combined gain of amplifier 12 and filter 18 is unity. When this condition is satisfied, within the frequency band of interest, the signal at output 16B of filter 16 is the same as the signal at input 12A of amplifier 12. Therefore, for signals within the frequency band of interest, no current flows through impedance 18 since there is no potential difference across impedance 18. Impedance 18 may be called a phantom impedance because, within the frequency band of interest, it is as if impedance 18 is not present.

It is desirable that the frequency response of filter 16 be relatively flat (constant) across the frequency band of interest. For many applications the frequency response should be flat to within ±0.5% across the frequency band of interest or ±0.1% in more demanding applications. It is also desirable that the gain of the combination of amplifier 12 and filter 16 be unity to a good level of precision within the frequency band of interest. In some embodiments the combined gain of filter 16 and amplifier 12 is 1±0.005 or 1±0.001 across a frequency band of interest (which may be, for example, the frequency band or a subset of the frequency band spanning 1 mHz to 1 KHz). The required tolerance will depend on the application.

In some embodiments the combined gain of amplifier 12 and filter 16 is unity to within a factor given by:

$$R_{18} \times 2\pi F C_{15}$$

where $R_{18}$ is the impedance of impedance 18 at the highest frequency, F, in the frequency band of interest, and $C_{15}$ is the capacitance of capacitor 15. So, for example, where impedance 18 is provided by a resistor having a resistance of 10 MΩ, and capacitor 15 has a value of 0.1 picoFarads and the maximum frequency of interest is 400 Hz then the combined gain of amplifier 12 and filter 16 in such embodiments is unity to within a factor of ±0.0027.

In some embodiments amplifier 12 and filter 16 both have a gain of one for signals in the frequency band of interest. This is preferred because there are well known constructions for amplifiers that maintain unity gain despite temperature variations and components that may be somewhat out of tolerance. It is more difficult to design an amplifier that will reliably maintain a particular non-unity gain. Nevertheless, in some alternative embodiments, amplifier 12 has a non-unity gain and filter 16 has a gain that is the inverse of the gain of amplifier 12 within the frequency band of interest.

It is desirable that amplifier 12 and filter 16 do not introduce a net phase shift in signals within the frequency band of interest. Especially for relatively low-frequency signals (e.g. signals having frequencies less than a few KHz) designing a filter and amplifier combination that does not materially shift phases of signals in a frequency band of interest is well within the level of routine skill in the art. If, for some reason, it is desired to use an amplifier 12 or filter 16 that may introduce a phase shift then the other one of amplifier 12 and filter 16 may be constructed in a way that introduces an equal and opposite phase shift or one or more additional circuit elements may be introduced to correct the phase shift.

Filter 16 may have a wide variety of constructions. In some embodiments filter 16 is a passive filter. In other embodiments filter 16 has active components. Filter 16 may be an analog filter or a digital filter. Filter 16 may be a high-pass filter or a bandpass filter. An example case where filter 16 is an analog filter with passive components is the case where filter 16 is an RC filter or a LRC filter. Especially where the lower end of the frequency band of interest is at a low frequency it is desirable for filter 16 to have a cut-off frequency that is below the low-frequency end of the frequency band of interest. In some embodiments filter 16 is a first-order high pass filter. In other embodiments filter 16 may be a second-order or higher-order filter.

In the ideal case, filter 16 has a flat frequency response for frequencies within the frequency band of interest and a frequency response that falls off at least for frequencies below the frequency band of interest.

Outside of the frequency band of interest, the signal at the output of filter 16 deviates from the signal at the input 12A of amplifier 12. For example, filter 16 may comprise a second-order filter having an output that converges toward a fixed electrical potential as the frequency decreases below a lower cut-off frequency. Any DC signal at input 12A of amplifier 12 that has a value that is different from the fixed electrical potential will see a relatively low-impedance path through impedance 18 and will equalize to the fixed electrical potential. By this mechanism, bias current may be supplied to amplifier 12 and charge imbalances at amplifier input 12A due to static electricity are neutralized while maintaining a high input impedance for signals within the frequency band of interest.

A signal may be taken from the output of filter 16 or from the output 12B of amplifier 12 for further processing. For example, the signal may be conditioned, further filtered, digitized by an analog-to-digital converter etc. The signal may be applied in any of a wide range of applications including applications such as monitoring signals present at sensor 14, determining physiological information about a subject by processing the signals, generating feedback signals, and the like.

The output of filter 16 may optionally be used to drive a low-impedance shield or shields 19. In some embodiments shield 19 may include a shield of one or more shielded cables connected to carry signals from sensor 14 to circuit 10. In such embodiments shield 19 is actively maintained at the same potential as the signal being detected for frequencies in the frequency band of interest. This reduces the pickup of electrical noise. Shield 19 may be arranged to shield sensor 14 and/or conductors connecting sensor 14 to amplifier 12 and/or amplifier 12 and/or filter 16. In an example embodiment, shield 19 shields a side of sensor 14, input capacitor 15, impedance 18, the input of amplifier 12 and a cable (if present) comprising a conductor connecting sensor 14 to the part of the circuit containing amplifier 12.

In some embodiments, impedance 18 comprises components in addition to a resistor 18A. For example, impedance 18 optionally provides a capacitor 18B in parallel to resistor 18A. Capacitor 18B may provide some protection against electrostatic discharges and may also provide a reduced-impedance path for high frequency signals.

As another example, impedance 18 may comprise a resistor 18A in parallel with one or more optional electrostatic discharge protection devices (ESDs) such as transient voltage suppression (TVS) diodes, Zener diodes, multilayer varistors, ceramic capacitors, or the like. For the same reasons as described above, these devices do not affect the input impedance of the circuit for signals within the frequency band of interest but provide low impedance paths which are available to dissipate voltages caused by electrostatic discharges. Electrostatic discharges tend to have very fast rise times (high frequencies). Filter 16 may block such high frequencies such that an electrostatic discharge results in a voltage across impedance 18 which can trigger the operation of an ESD. An ESD 18C is illustrated.

It is not mandatory that the resistive component of impedance 18 be provided by a discrete resistor 18A. In some embodiments impedance 18 is provided by a device that provides an electrical resistance between the output of filter 16 and input 12A of amplifier 12 and also provides other functionality.

Figure 1A:
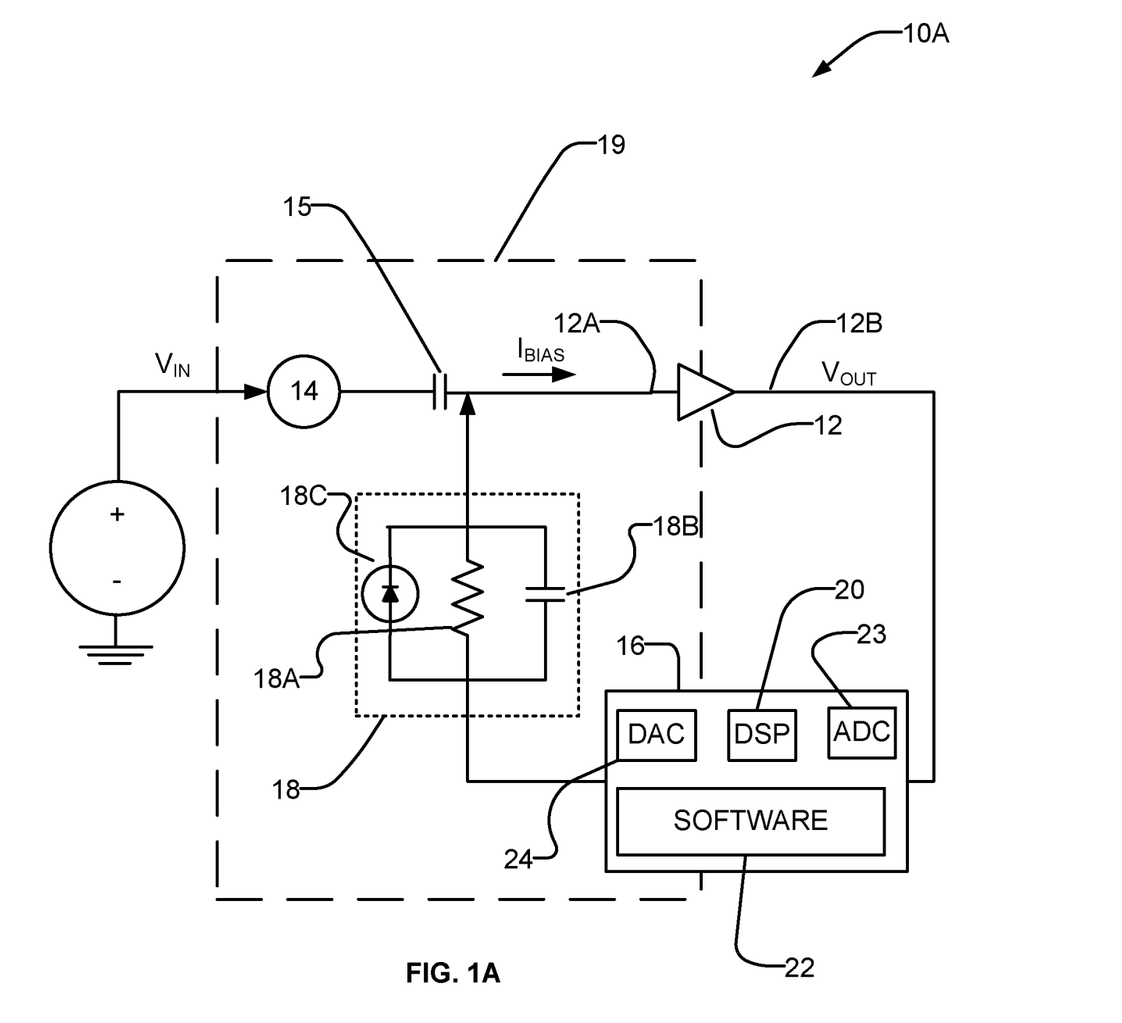
FIG. 1A is a circuit diagram illustrating an example single sensor system using a digital filter and digital-to-analog converter.

In some embodiments, filter 16 is implemented as a digital filter, for example within a digital signal processor (DSP) programmed to provide a variable gain. FIG. 1A illustrates an example circuit 10A according to an embodiment in which filter 16 is implemented by a DSP 20 executing software instructions 22. The analog output signal $V_{OUT}$ from amplifier 12 is converted to digital format by analog-to-digital converter (ADC) 23. The digital signal is processed by DSP 20. The digital output of DSP 20 is converted to analog by a digital-to-analog converter (DAC) 24 and applied to impedance 18 which operates as described above.

In some embodiments filter 16 has a variable gain within the frequency band of interest. The gain of filter 16 may be actively controlled to maintain a gain that is the inverse of the gain of amplifier 12. In the embodiment of FIG. 1A, DSP 20 may be configured by software 22 to measure the gain of amplifier 12. For example, circuit 10A may be configured to generate a test signal having a known amplitude and a frequency outside of (e.g. just above) the frequency band of interest. The test signal may be generated by a separate oscillator or signal generator but it is convenient to program DSP 20 to generate the test signal and to apply the test signal at its output.

DSP 20 is configured to detect the test signal at the output of amplifier 12 and to determine the gain of amplifier 12 by comparing the initial amplitude of the test signal to the amplitude of the amplified test signal at the output of amplifier 12. DSP 20 may then adjust the gain of filter 16, as and if necessary, to be the inverse of the measured gain of amplifier 12.

The amplitude of the test signal may be regulated to have a desired known value but this is not mandatory since DSP 20 may optionally be configured to measure the amplitude of the initial test signal 12 using an analog-to-digital converter (ADC).

Figure 2:
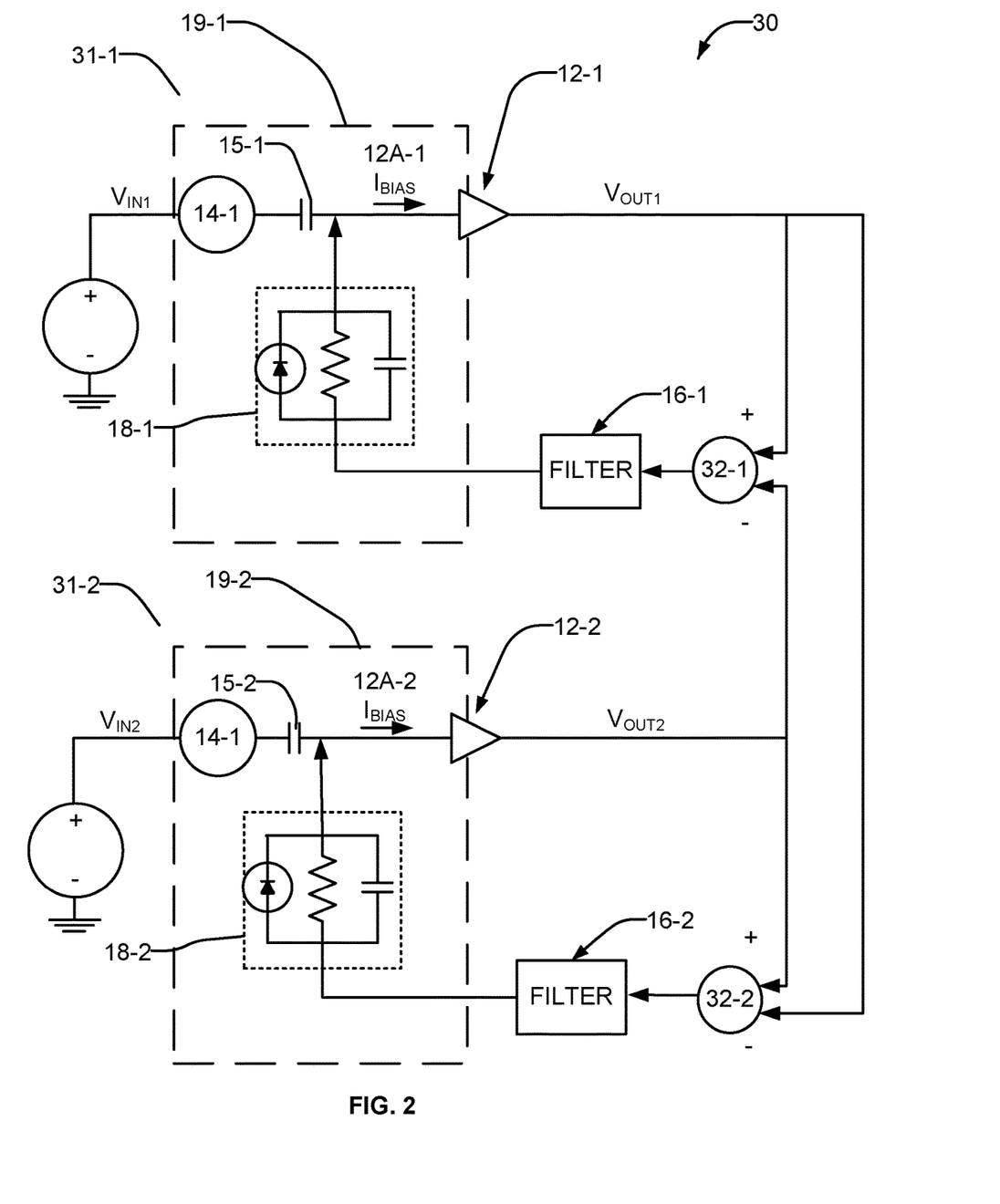
FIG. 2 is a circuit diagram for an example embodiment having two sensors connected in a differential configuration.

FIG. 2 shows another example circuit 30 which provides two sensor circuits 31-1 and 31-2 connected in a differential configuration. In FIG. 2 elements that are the same as or similar to elements that are depicted in FIG. 1 have the same reference numbers except that the suffixes '-1' and '-2' are added to indicate which sensor circuit (31-1 or 31-2) the element is part of. These suffixes may be omitted when discussing the elements generally. Each sensor circuit 31 comprises an amplifier 12, a filter 16 and an impedance 18, all of which may be as described herein.

Circuits 31-1 and 31-2 differ from circuits 10 and 10A described above in that they each include a difference circuit 32 having inputs connected to receive output signals from amplifiers 12-1 and 12-2 and an output connected to the corresponding filter 16. Difference circuits 32 may be implemented in the digital or analog domains. Where filters 16 are implemented digitally it can be convenient to implement difference circuits 32 in the same processor(s) (e.g. DSP) used to implement filters 16.

In operation, a first voltage signal ($V_{IN1}$) is detected at sensor 14-1 and applied at the input of amplifier 12-1 by way of capacitor 15-1. A second voltage signal ($V_{IN2}$) is detected at sensor 14-2 and applied at the input of amplifier 12-2 by way of capacitor 15-2. In response, output voltages $V_{OUT1}$ and $V_{OUT2}$ are respectively presented at outputs of amplifiers 12-1 and 12-2.

Differential circuit 32-1 determines the difference between $V_{OUT1}$ and $V_{OUT2}$ and applies that difference to the input of filter 16-1. Differential circuit 32-2 determines the difference between $V_{OUT2}$ and $V_{OUT1}$ and applies that difference to the input of filter 16-2. A gain of ½ is provided in differential circuits 32 or in filters 16 such that the signal at the output of filter 16-1 is given by:

$$V_{16-1} = V_{IN-1} - V_{AVG} \qquad (1)$$
$$= V_{IN1} - \frac{V_{IN1} + V_{IN2}}{2}$$
$$= \frac{V_{IN1}}{2} - \frac{V_{IN2}}{2}$$

where $V_{16-1}$ is the signal at the output of filter 16-1, $V_{IN1}$ and $V_{IN2}$ are as described above, and $V_{AVG}$ is the average of $V_{IN1}$ and $V_{IN2}$. The signal at the output of filter 16-2 is given by a similar relationship except that $V_{IN1}$ and $V_{IN2}$ are interchanged.

Since signals common to sensor circuits 31-1 and 31-2 are eliminated by differential circuits 32, these common signals are absent from the outputs of filters 16-1 and 16-2. The absence of the common signals at the outputs of filters 16 causes impedance 18-1 and 18-2 to provide a relatively low impedance path for the common signals. The effect is that the common signals are rejected by circuit 30. Additionally, the gain of sensor circuits 31-1 and 31-2 for the common signals is very low so that the presence of common components in $V_{IN1}$ and $V_{IN2}$ does not push the output of either of amplifiers 12 to its limits. Circuit 30 behaves is if it has a driven ground connection to the subject but does not require a separate physical ground connection to the subject (although such a ground connection may optionally be present). Circuit 30 may be said to provide a virtual driven ground.

Difference signals from first and/or second sensor circuits 31-1 and 31-2 may be processed for an intended application. The difference signals may be obtained at the output of one of filters 16-1 and 16-2 or one of differential circuits 32-1 and 32-2. In the alternative, a separate difference circuit may determine the difference between the outputs of amplifiers 12-1 and 12-2 to yield a difference signal that may be provided to a data processor e.g. a programmable processor such as a DSP, microprocessor, embedded processor or the like or a logic circuit such as a hard-wired logic circuit, custom logic chip (e.g. an ASIC), suitably-configured configurable logic (e.g. a configured field programmable gate array—FPGA), or suitable combinations of these.

Figure 3:
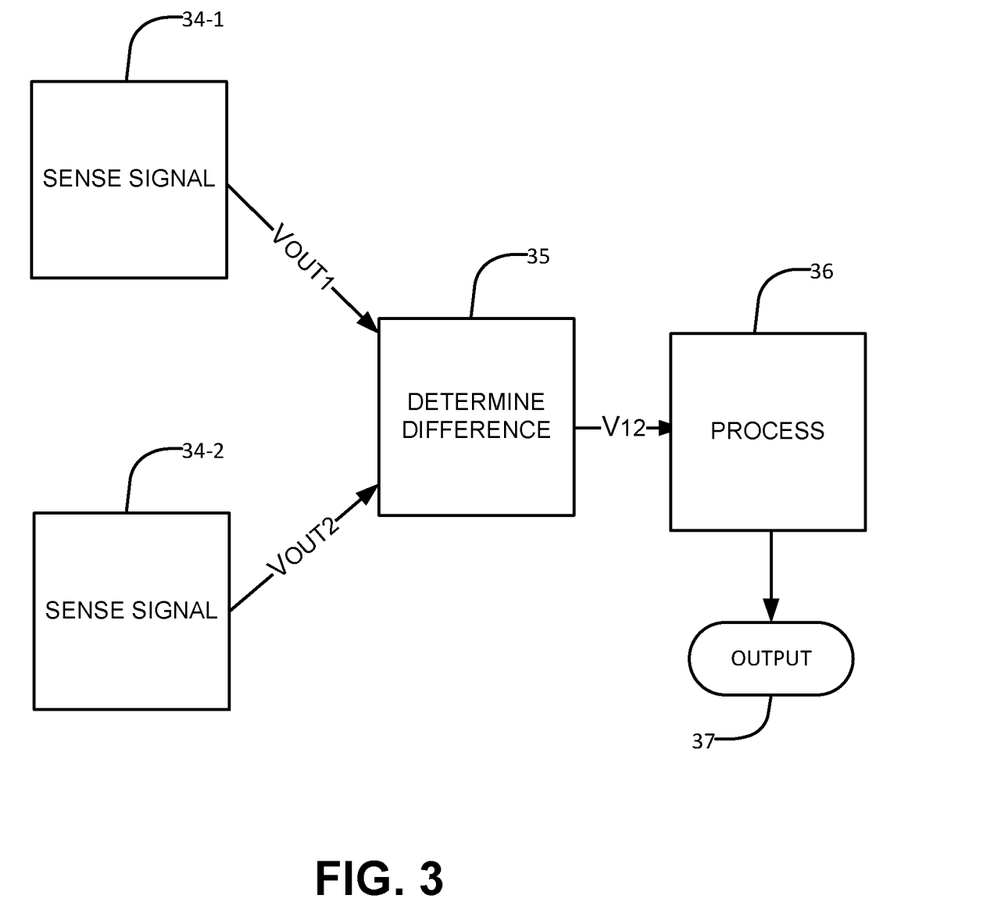
FIG. 3 is a block diagram illustrating a system having two sensors connected in a differential configuration.

FIG. 3 shows an example case where outputs $V_{OUT1}$ and $V_{OUT2}$ respectively obtained at blocks 34-1 and 34-2 by sensing signals using circuits as described herein (e.g. using sensor circuits 31-1 and 31-2) are subtracted at block 35 to yield a difference signal $V_{12}$. Block 35 may be implemented using an analog difference circuit or may comprise a numerical subtraction step performed after digitization of $V_{OUT1}$ and $V_{OUT2}$. Difference signal $V_{12}$ is processed in block 36. Block 36 may comprise processing difference signal $V_{12}$ according to algorithms implemented in a data processor, logic circuits or the like to produce an output 37. In some embodiments output 37 is a feedback signal that is detectable (consciously or sub-consciously) by a human sensory system such as the auditory system or the visual system or the tactile system. In some embodiments the output comprises a modulation or other modification to sounds being presented to a subject.

In some embodiments, one or more electrodes for one or more sensors is provided by a layer in a printed circuit board. An electrically-conducting shield electrically insulated from the electrode may be provided by another layer of the printed circuit board. The shield and electrode may, for example, be separated by a non-conducting layer of the printed circuit board. The shield in some embodiments is larger than and overlaps with edges of the electrode. In embodiments which provide an electrode in a printed circuit board, a sensor circuit may be provided on the same printed circuit board. In such embodiments the sensor circuit may be connected to the electrode and to a shield, if present, by conductive elements of the printed circuit board. In some embodiments the printed circuit board is flexible. In such embodiments the printed circuit board may be flexed to cause a curvature in the electrode that matches a curvature of a portion of a subject such as a person.

Figure 4:
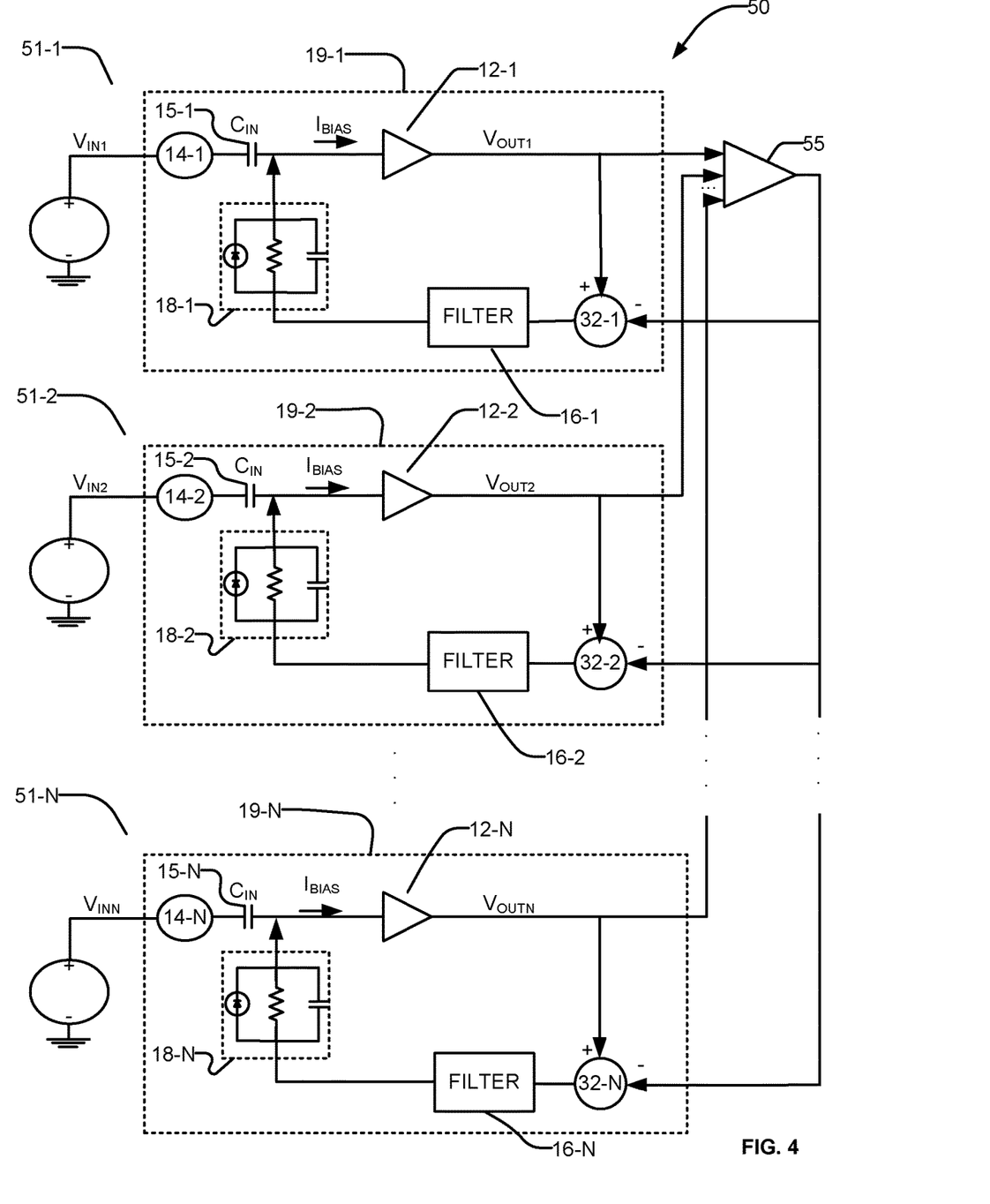
FIG. 4 is a circuit diagram illustrating an example sensor system having a plurality of sensors and a virtual driven ground.

In some embodiments it may be desirable to provide a system that includes more than one or two sensors. The sensors may be arranged in differential pairs or not. FIG. 4 shows an example circuit 50 comprising a plurality of sensor circuits 51-1, 51-2, . . . 51-N. Circuit 50 may include any reasonable number of sensor circuits 51. Each sensor circuit 51 may be similar to sensor circuit 10 or 10A as described above. Circuit 50 differs from the circuits described above in the signals input to filters 16.

In circuit 50, the input to each filter 16 comprises a combination of the output of the corresponding amplifier 12 with a representative signal based on the outputs of one or more other ones of amplifiers 12. The representative signal may have a value such as an average, mean or median that is representative of the collective outputs of amplifiers 12. The representative signal may be subtracted from the output of the corresponding amplifier 12. The output of each amplifier 12 may then be the difference between the corresponding input signal (e.g. $V_{IN1}$) and the representative signal. This may be advantageous in cases where the absolute magnitudes of measured signals are not important but the relationships between the measured signals is what is important.

A combining circuit may be connected between the output of the amplifier and the input of the filter to generate the signal that is input to the filter. In some embodiments the combining circuit comprises a difference (subtraction) circuit. Combining may be performed in the analog or digital domains. In some embodiments a difference circuit is configured to subtract from the amplifier output signal a function of the output signals from the additional signal sensors.

In an example embodiment, the input to filter 16-1 is given by:

$$V_{FILTER1} = V_{OUT1} - K \frac{1}{N} \sum_{i=1}^{N} V_{OUTi} \qquad (2)$$

where K is a constant. K, for example, has a value in the range of 0.1 to 20. In some embodiments K=1. Inputs to other filters 16 are provided by the same equation (2) modified by replacing $V_{OUT1}$ with the output signal from the corresponding amplifier 12.

The average provided by the second term on the right hand side of equation (2) may optionally be a weighted average given, for example, by:

$$\frac{1}{N} \sum_{i=1}^{N} C_i V_{OUTi}$$

where $C_i$ are weighting factors that may, in general, be different for different values of i.

Circuit 50 includes an averaging circuit 55 that corresponds to the second term on the right-hand side of equation (2). Difference circuits 32 in each sensor circuit 51 are connected to subtract the output of averaging circuit 55 from the output of the corresponding amplifier 12. For example, difference circuit 32-1 in sensor circuit 51-1 is connected to subtract the output of averaging circuit 55 from the output of amplifier 12-1. Averaging circuit 55 may be implemented as an analog circuit, as a digital process or as a combination thereof.

The output of each sensor circuit 51 in circuit 50 is indicative of the difference between the signal $V_{IN}$ picked up by that circuit 50 and the representative signal value (e.g. the average output of all of sensor circuits 51). Thus circuit 50 provides an output similar to a circuit that provides a ground that is connected to the subject and driven by the representative signal (e.g. to have a potential equal to the average of the sensed signals).

In some embodiments the representative signal is constructed from the filtered signals (e.g. the signals at the outputs of filters 16) instead of the signals at the outputs of amplifiers 12 as shown in FIG. 4.

Figure 5:
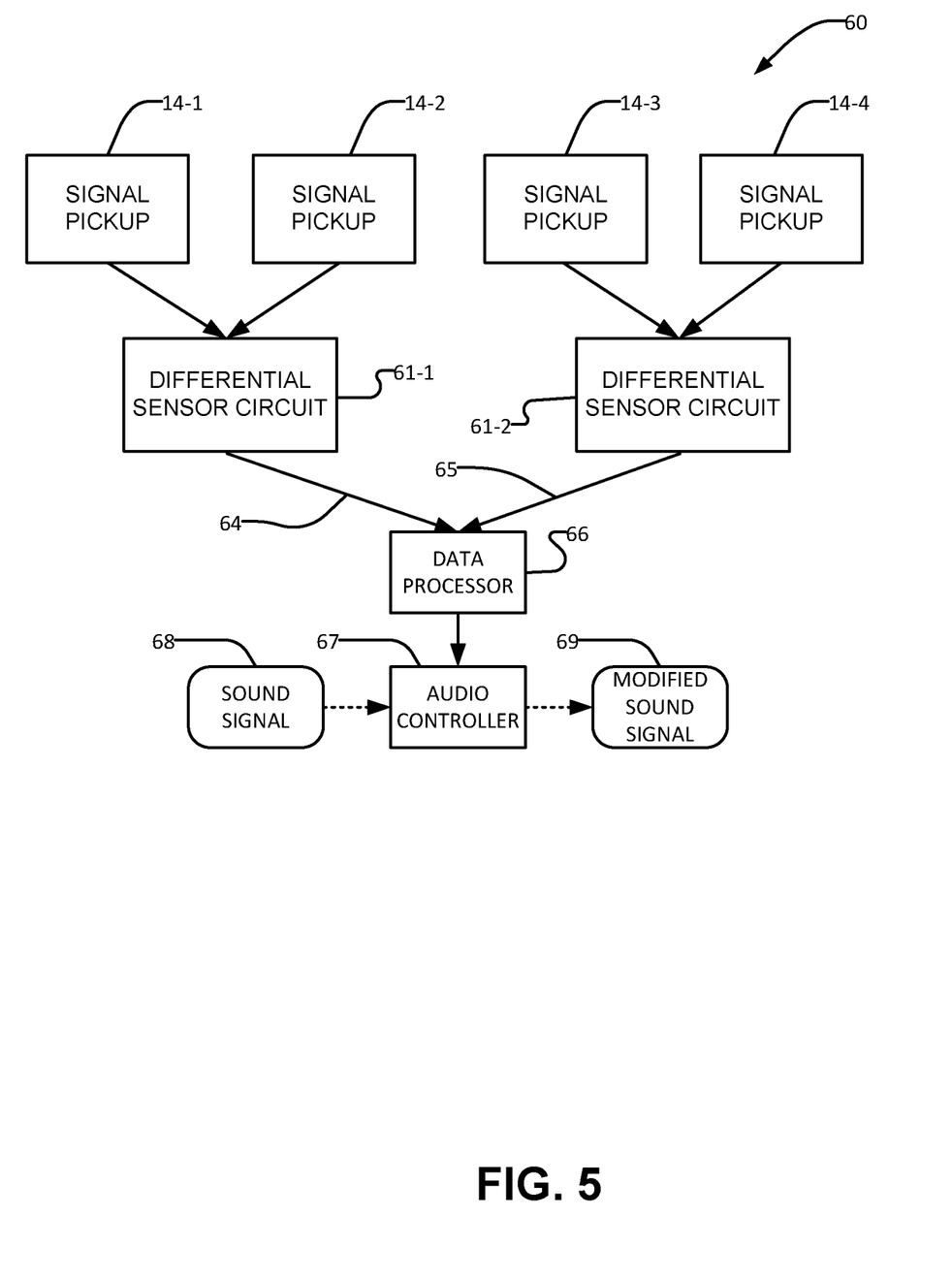
FIG. 5 is a block diagram illustrating a neurosensing system including capacitive sensors according to an example embodiment of the present technology.

While the sensor circuits as described herein have a very wide range of applications, one application of particular interest to the inventors is biosensing and particularly neurosensing. FIG. 5 illustrates an example neurosensing system 60 comprising at least four sensors, 14-1, 14-2, 14-3 and 14-4. Signal sensors 14-1 and 14-2 are connected to a differential sensor circuit 61-1. Signal sensors 14-3 and 14-4 are connected to a differential sensor circuit 61-2.

Sensor circuit 61-1 is configured to output a difference signal representing the difference between signals picked up by sensors 14-1 and 14-2. Similarly, sensor circuits 61-2 is configured to output a difference signal representing the difference between signals picked up by sensors 14-3 and 14-4. Sensors 14-1 and 14-2 may be located to detect signals on one side of a subject's head (e.g. the left side) while sensors 14-3 and 14-4 may be located to detect signals on the other side of the subject's head (e.g. the right side). The resulting right and left difference signals 64, 65 are directed to a data processor 66 executing an algorithm that processes the difference signals and generates feedback to be delivered to the subject.

For example, data processor 66 may analyze signals 64 and 65 to evaluate balance between the subject's left brain activity and right brain activity. Data processor 66 may then issue control signals to an audio controller 67 to modify a sound signal 68 to yield a modified sound signal 69 which may be delivered by audio controller 67 to the subject. For example, audio controller 67 may be controlled to insert audio dropouts into sound signal 68 if there is an imbalance detected between the subject's left-brain and right-brain activity levels.

Figure 6:
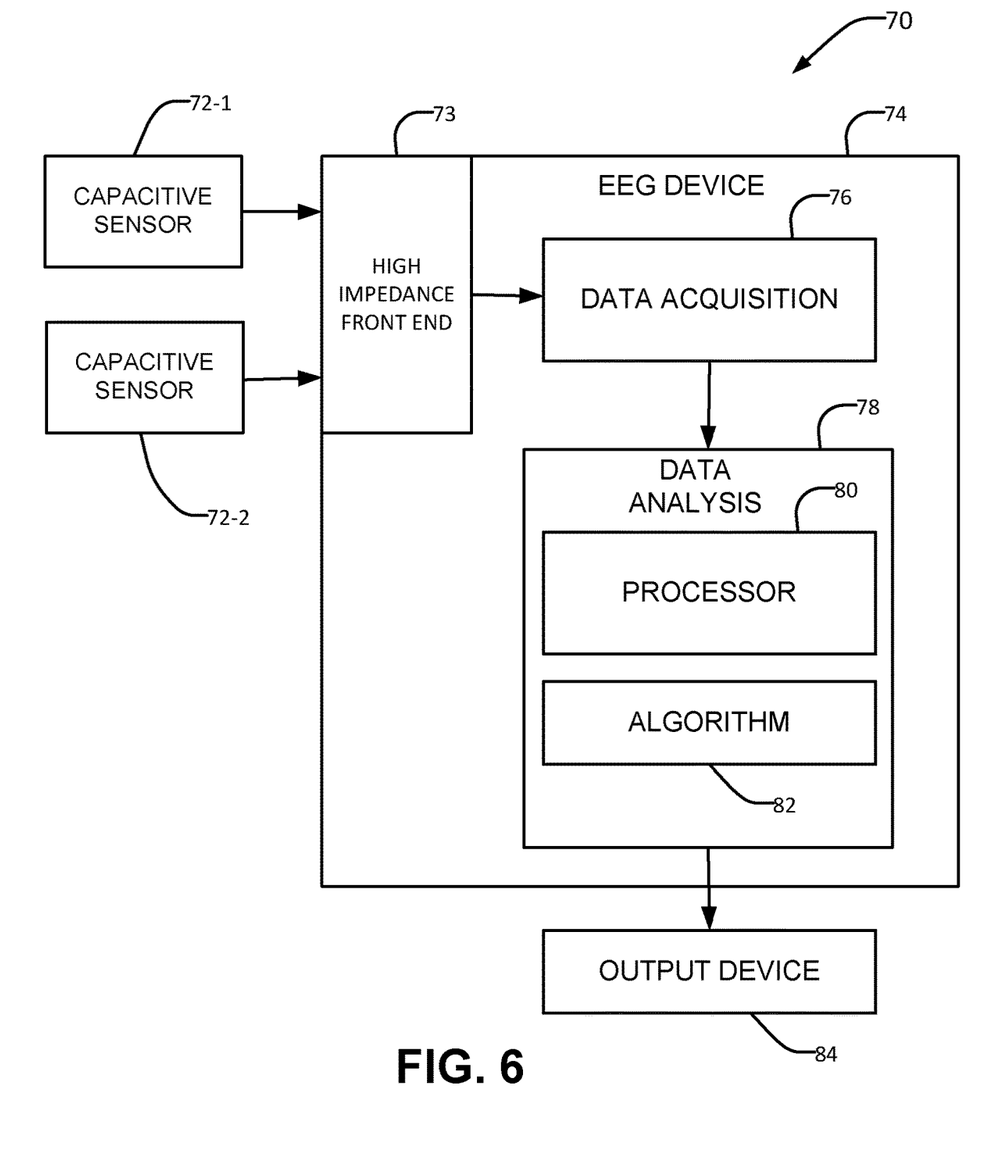
FIG. 6 is a block diagram illustrating an example biofeedback system incorporating high input impedance signal detectors as described herein.

FIG. 6 shows a system 70 according to another example embodiment. System 70 comprises at least two capacitive sensors 72-1 and 72-2 which sense the charge on the skin or scalp of a user. A capacitive sensor is a sensor that does not rely on low-impedance electrical conduction to pick up signals from a subject. A capacitive sensor provides an electrode that is capacitively coupled to the subject's skin (the scalp in some embodiments). It is possible but not mandatory for the electrode of the capacitive sensor to be electrically insulated from the subject's skin, for example by a layer of a dielectric material.

Capacitive sensors 72 and 72 are connected to a device 74 which detects and processes signals picked up by capacitive sensors 72. Device 74 comprises a high impedance front end 73 that incorporates one or more sensor circuits as described herein In system 70, device 74 comprises an EEG device that includes a data acquisition module 76 and a data analysis module 78, which may be provided by a data processor 80 executing an algorithm 82. Data analysis module 78 controls an output device 84. Output device 84 may include one or more devices of any of a wide variety of types including output devices such as a display, a printer, a sound generator, a data logger a digital or analog control signal for another device etc.

In some embodiments, the same processor is applied to both: perform digital filtering as described for example with reference to FIG. 1A and to process detected signals.

In an example embodiment, as EEG data are acquired by way of capacitive sensors 72, information about the brain's performance is calculated by signal processing algorithm 82 in the data analysis module 78. Imbalances detected between activity of the right and left sides of the brain of a subject results in signal processing algorithm 82 determining an imbalance, and the processor 80 signaling output device 84 to modify a sound signal being played to the subject (e.g. by inserting one or more auditory drop outs into the sound signal). The sound signal comprises a music signal in some embodiments.

In a neurofeedback system according to an example embodiment, one or more circuits as described herein are mounted to a headset which also supports potential-sensing contacts coupled to inputs of the amplifiers. The headset may be worn such that EEG signals detected at the potential-sensing contacts are amplified by amplifiers 12. In some embodiments the headset supports at least one first pair of potential-sensing contacts for contacting the left-side of a person's scalp when the headset is being worn and at least one second pair of potential-sensing contacts for contacting the left-side of a person's scalp when the headset is being worn.

The potential-sensing contacts may comprise electrodes, non-contact sensors, high-impedance sensors or the like. In some embodiments the potential-sensing contacts have DC impedances in excess of 1 M$\Omega$ or in excess of 10 M$\Omega$. In some embodiments the potential-sensing contacts are capacitively coupled to the inputs of corresponding amplifiers 12 (e.g. by capacitors 15).

Another aspect of the invention provides methods for detecting electrical potentials. One aspect comprises coupling an electrical potential to the input of an amplifier, at an output of the amplifier detecting an amplifier output signal comprising a signal of interest; extracting the signal of interest from the amplifier output signal; and applying the extracted signal of interest to one end of an impedance having a second end connected to the amplifier input. In some embodiments the signal of interest is a signal within a specified frequency band. In such embodiments, extracting the signal of interest may comprise filtering the amplifier output signal in a bandpass filter or a low-pass filter. In some embodiments the signal of interest comprises a difference between signals representing potentials measured at two locations. In such embodiments extracting the signal of interest may comprise subtracting another signal from the amplifier output signal. Some embodiments comprise supplying a DC bias current for the amplifier by way of the impedance.

Amplifiers 12 in the circuits described above can be conveniently provided by integrated operational amplifiers (op amps) although this is not mandatory. Operational amplifiers having very high input impedances and low bias current requirements are commercially available. It is not mandatory that the amplifiers, filters and difference circuits described herein be separate and discrete from one another. These elements may share components. For example, an amplifier may have bandpass characteristics that provide the described filtering function—in which case a separate filter may not be present or required. In embodiments where two amplifiers are shown connected to provide a differential output alternative embodiments may use a single differential amplifier with separate feedback paths for each input.

Advantages of the exemplary embodiments described herein may be realized and attained by means of the instrumentalities and combinations particularly pointed out in this written description. It is to be understood that the foregoing general description and the following detailed description are exemplary and explanatory only and are not restrictive of the claims below. While example embodiments have been described in detail, the foregoing description is in all aspects illustrative and not restrictive. It is understood that numerous other modifications and variations can be devised without departing from the scope of the example embodiment.

It is to be understood that the invention is not limited to the specific disclosed example embodiments. Those skilled in the art will recognize, or be able to ascertain using no more than routine experimentation, many modifications of and equivalents to the specific example embodiments described herein. Such equivalents are intended to be encompassed in the scope of the claims, if appended hereto or subsequently filed. For example, in another embodiment, the single sensor circuit is implemented with only one amplifier providing that its frequency response is non-unity below the band of interest. Similarly, if the amplifier is a differential amplifier then the dual sensor can be implemented without the differential circuit. Additionally if the amplifier's frequency response is non-unity below the bandwidth of interest the single or dual sensor can be implemented without filter 16.

Interpretation of Terms

Unless the context clearly requires otherwise, throughout the description and the claims:

"comprise", "comprising", and the like are to be construed in an inclusive sense, as opposed to an exclusive or exhaustive sense; that is to say, in the sense of "including, but not limited to";

"connected", "coupled", or any variant thereof, means any connection or coupling, either direct or indirect, between two or more elements; the coupling or connection between the elements can be physical, logical, or a combination thereof;

"herein", "above", "below", and words of similar import, when used to describe this specification, shall refer to this specification as a whole, and not to any particular portions of this specification;

"or", in reference to a list of two or more items, covers all of the following interpretations of the word: any of the items in the list, all of the items in the list, and any combination of the items in the list;

all words used herein shall be construed to be of such gender or number (singular or plural) as the circumstances require;

the singular forms "a", "an", and "the" also include the meaning of any appropriate plural forms unless the context clearly dictates otherwise;

descriptive headings are for convenience only and shall not control or affect the meaning or construction of any part of the specification;

"or" and "any" are not exclusive and "include" and "including" are not limiting unless the context clearly dictates otherwise.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Embodiments of the invention may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs")). Examples of programmable data processors are: microprocessors, digital signal processors ("DSPs"), embedded processors, graphics processors, math co-processors, general purpose computers, server computers, computer workstations, and the like. For example, one or more data processors in a biofeedback device may implement methods as described herein by executing software instructions in a program memory accessible to the processors.

Recitation of ranges of values herein are merely intended to serve as a shorthand method of referring individually to each separate value falling within the range, unless otherwise indicated herein, and each separate value is incorporated into the specification as if it were individually recited herein. Where a specific range of values is provided, it is understood that each intervening value, to the tenth of the unit of the lower limit unless the context clearly dictates otherwise, between the upper and lower limit of that range and any other stated or intervening value in that stated range, is included therein. All smaller sub ranges are also included. The upper and lower limits of these smaller ranges are also included therein, subject to any specifically excluded limit in the stated range.

Unless defined otherwise, all technical and scientific terms used herein have the same meaning as commonly understood by one of ordinary skill in the relevant art. Although any methods and materials similar or equivalent to those described herein can also be used, the acceptable methods and materials are now described.

All methods described herein can be performed in any suitable order unless otherwise indicated herein or otherwise clearly contradicted by context. The use of any and all examples, or exemplary language (e.g., "such as") provided herein, is intended merely to better illuminate the example embodiments and does not pose a limitation on the scope of the claimed invention unless otherwise claimed. No language in the specification should be construed as indicating any non-claimed element as essential.

Specific examples of systems, methods and apparatus have been described herein for purposes of illustration. These are only examples. The technology provided herein can be applied to systems other than the example systems described above. For example, such systems may be applied to sensing all manner of bioelectric signals. Such signals may be applied for example for monitoring function of the brain, heart, and other organs. In addition to other applications, the present technology may be applied in medical devices such as prosthetics, assistive devices, cardiac monitors and myography devices and related methods; sleep and alertness monitoring; game, digital appliance and computer interaction; control of vehicles and equipment; fitness devices which include physiological monitoring functions and so on. The technology also has application in sensing signals of non-biological origin. Sensing circuits as described herein may be supported by and/or integrated into clothing, headwear, helmets or the like or surfaces that are touched by or adjacent to body parts of persons or animals when in use (such as handles, knobs, surfaces of furniture such as chairs, beds, seats, headrests, medical probes, or the like).

Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

What is claimed is:

1. An apparatus for measuring electrical potentials in a frequency band, the apparatus comprising:
    an amplifier having a first gain, an input and an output;
    a filter having a second gain inverse the first gain, and an input connected to receive a signal from the amplifier output and an output; and
    one or more circuit elements that provide an electrical impedance having a resistive component coupled between the filter output and the amplifier input;
    wherein the filter has a passband that includes the frequency band and excludes direct current signals and the amplifier and filter combined have unity gain for signals in the frequency band.

2. The apparatus according to claim 1 further comprising a capacitor coupling the input of the amplifier to a signal source.

3. The apparatus according to claim 2 wherein the one or more circuit elements comprise a resistor.

4. The apparatus according to claim 3 wherein the one or more circuit elements comprise a capacitor connected in parallel with the resistor.

5. The apparatus according to claim 3 wherein the one or more circuit elements comprise an electrostatic discharge protection device connected in parallel with the resistor.

6. The apparatus according to claim 1 wherein the filter has a flat frequency response within the frequency band.

7. The apparatus according to claim 1 wherein the filter is a high-pass filter.

8. The apparatus according to claim 1 wherein the filter is a bandpass filter.

9. The apparatus according to claim 1 wherein the filter provides bias current to the amplifier by way of the one or more circuit elements.

10. The apparatus according to claim 1 wherein the frequency band comprises the frequencies in the range of 1 Hz to 100 Hz.

11. The apparatus according to claim 1 wherein the frequency band comprises the frequencies in the range of 100mHz to 300 Hz.

12. The apparatus according to claim 1 wherein the amplifier is an operational amplifier.

13. The apparatus according to claim 1 wherein the filter comprises a digital filter.

14. The apparatus according to claim 13 further comprising an analog-to-digital converter configured to digitize the signal from the amplifier output, a digital signal processor configured to digitally filter the digitized signal to yield a digitized filtered signal and a digital-to-analog converter configured to convert the digitized filtered signal to an analog filtered signal, the digital-to-analog converter having an output coupled to the amplifier input to apply the analog filtered signal to the amplifier input by way of the one or more circuit elements.

15. The apparatus according to claim 1 further comprising a low-impedance shield connected to the output of the filter and arranged to shield at least one of the input of the amplifier and the one or more circuit elements.

16. The apparatus according to claim 1 further comprising a neurofeedback system operative to receive and process a signal from the output of the amplifier or the filter.

17. The apparatus according to claim 1 further comprising a signal sensor coupled to the input of the amplifier.

18. The apparatus according to claim 17 wherein the signal sensor comprises an electrode.

19. The apparatus according to claim 17 wherein the signal sensor has an impedance of at least 1 MΩ within the frequency band.

20. The apparatus according to claim 17 wherein the signal sensor comprises a capacitive sensor.

21. The apparatus according to claim 1 further comprising a combining circuit connected between the output of the amplifier and the input of the filter, the combining circuit providing to the input of the filter a signal that combines an amplifier output signal from the amplifier and output signals from one or more additional signal sensors.

22. The apparatus according to claim 1 wherein the amplifier is mounted on a printed circuit board and the printed circuit board comprises an electrode electrically coupled to the input of the amplifier.

23. The apparatus according to claim 22 wherein the printed circuit board is a multi-layer printed circuit board and the printed circuit board provides an electrically conductive shield connected to the output of the filter, the electrically-conductive shield electrically insulated from and physically overlapping with the electrode.

24. The apparatus according to claim 23 wherein the electrode and shield are respectively formed on first and second different layers of the printed circuit board.

25. The apparatus according to claim 1 wherein the first gain is non-unity.

26. An apparatus for measuring electrical potentials in a frequency band of interest, the apparatus comprising:
    an amplifier having an input and an output;
    a filter having an input connected to receive a signal from the amplifier output and an output;
    one or more circuit elements that provide an electrical impedance having a resistive component coupled between the filter output and the amplifier input; and
    a combining circuit connected between the output of the amplifier and the input of the filter, the combining circuit providing to the input of the filter a signal that combines an amplifier output signal from the amplifier and output signals from one or more additional signal sensors;
    wherein the filter has a passband that excludes direct current signals and the amplifier and filter combined have unity gain for signals in a frequency band within the passband of the filter; and
    wherein the combining circuit comprises a difference circuit configured to subtract from the amplifier output signal a function of the output signals from the additional signal sensors.

27. The apparatus according to claim 26 wherein the function of the output signals from the additional signal sensors comprises an average.

28. A method for detecting electrical potentials comprising:

at an output of an amplifier having a first gain and an electrical potential applied to an input of the amplifier, detecting an amplifier output signal comprising a signal of interest;

extracting the signal of interest from the amplifier output signal using a filter that has a second gain that is inverse the first gain and a passband that excludes direct current signals; and applying the extracted signal of interest to one end of an impedance load having a second end connected to the input of the amplifier;

wherein the impedance load comprises one or more circuit elements that provide an electrical impedance.

29. The method according to claim 28 wherein the signal of interest is a signal within a specified frequency band within the passband of the filter.

30. The method according to claim 28 wherein the signal of interest comprises a difference between signals representing potentials measured at two locations and extracting the signal of interest comprises subtracting another signal from the amplifier output signal.

31. The method according to claim 28 further comprising supplying a DC bias current for the amplifier by way of the impedance load.

32. The method according to claim 28 wherein the first gain is non-unity.

* * * * *